(12) United States Patent
Doll et al.

(10) Patent No.: US 8,182,492 B2
(45) Date of Patent: May 22, 2012

(54) MEDICAL INSTRUMENT, ESPECIALLY UTERUS MANIPULATOR

(75) Inventors: Frank Doll, Talheim (DE); Martin Hahn, Boll (DE)

(73) Assignee: Karl Storz GmbH & Co. KG (DE)

( * ) Notice: Subject to any disclaimer, the term of this patent is extended or adjusted under 35 U.S.C. 154(b) by 1853 days.

(21) Appl. No.: 11/113,162

(22) Filed: Apr. 22, 2005

(65) Prior Publication Data
US 2006/0241652 A1 Oct. 26, 2006

(51) Int. Cl.
*A61B 17/42* (2006.01)
(52) U.S. Cl. .......................... 606/119; 606/147; 606/208
(58) Field of Classification Search .................. 606/119, 606/147, 208
See application file for complete search history.

(56) References Cited

U.S. PATENT DOCUMENTS

| | | | | |
|---|---|---|---|---|
| 4,022,208 A | * | 5/1977 | Valtchev | 604/515 |
| 5,306,275 A | * | 4/1994 | Bryan | 606/61 |
| 5,445,643 A | | 8/1995 | Valtchev | 606/119 |
| 5,562,679 A | | 10/1996 | Valtchev | 606/119 |
| 6,244,759 B1 | * | 6/2001 | Russo | 396/428 |

* cited by examiner

*Primary Examiner* — Gary Jackson
*Assistant Examiner* — Eric Blatt
(74) *Attorney, Agent, or Firm* — St. Onge Steward Johnston & Reens LLC

(57) ABSTRACT

A medical instrument, especially a uterus manipulator, comprises a shaft, an actuator movable relative to said shaft in order to move a tool and a locking device to lock the actuator relative to the shaft. It is now proposed that the locking device comprises a clamping element which is slidably arranged therein.

10 Claims, 5 Drawing Sheets

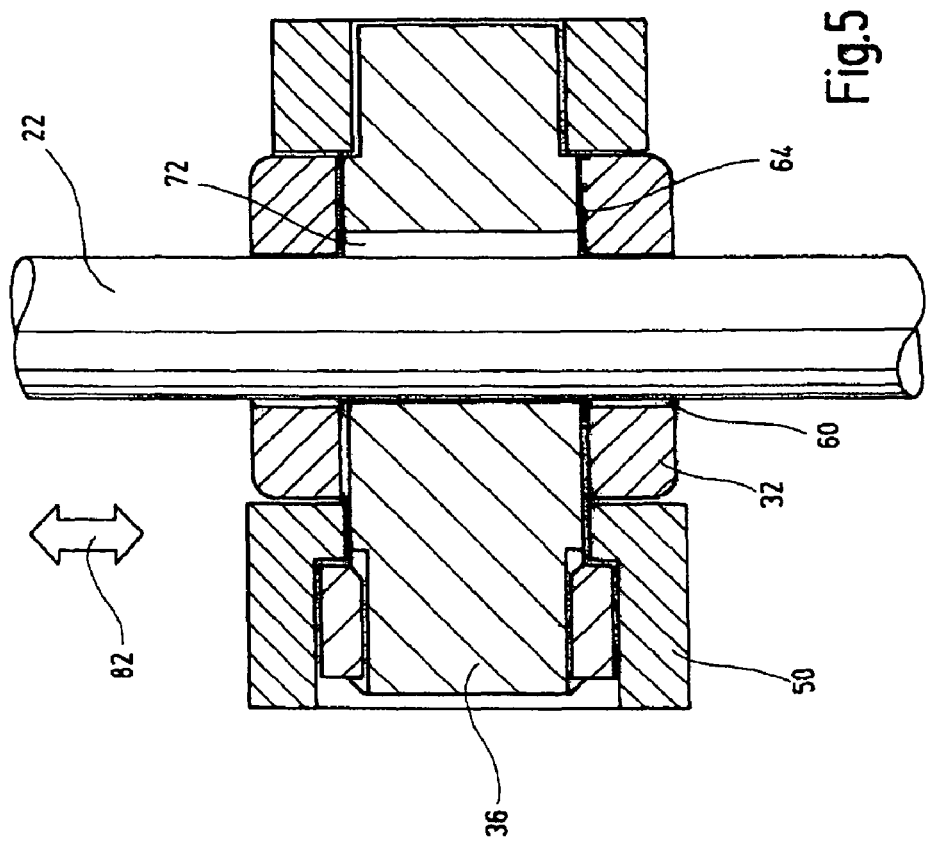

MEDICAL INSTRUMENT, ESPECIALLY UTERUS MANIPULATOR

FIELD OF THE INVENTION

The present invention relates to a medical instrument comprising a shaft having a distal and a proximal end, a tool at the distal end of the shaft, a grip at the proximal end of the shaft, an actuator with which the tool is movable, and a locking device comprising a handle and a clamping element, the clamping element being movable by the handle between a first and a second position, whereby in the first position of the clamping element the actuator is freely movable, and in the second position of the clamping element the actuator is locked in the locking device.

Such a medical instrument is, for example, a uterus manipulator.

A uterus manipulator is used among other things to move the uterus to a desired position during laparoscopic examinations in the abdomen of a female patient. This is done, for example, in order to examine a concealed part of the uterus or to move the uterus out of an area which is to be examined or treated by laparoscopic means.

RELATED PRIOR ART

Such a uterus manipulator is, for example, known from U.S. Pat. No. 4,022,208.

This document discloses a uterus manipulator comprising a shaft, at the distal end of which a tool is arranged which is movable by an actuator. The uterus manipulator known from this document further comprising a locking device with which the actuator can be locked relative to the shaft. The locking device in this case is constituted by a locking screw which in closed position pushes against the actuator, thereby locking the actuator within the locking device. The handle is constituted by the head of the locking screw, the clamping element by the body of the screw.

Such a construction has the disadvantage that an operator needs two hands in order to lock the locking device in a desired position of the tool because the use of a screw makes it very difficult to hold the actuator in a desired position relative to the shaft and to close the locking device at the same time.

Further it turned out that while tightening the screw, especially during the final tightening, the uterus manipulator whose tool is already inserted into the uterus of the patient is often being twisted, whereby at the tool end large amounts of pressure are applied to the tissue. Such pressure can lead to injuries to the uterus.

SUMMARY OF THE INVENTION

It is, therefore, an object of the present invention to describe a medical instrument whose locking device is easier to use.

According to the invention, the object is achieved by the fact that the clamping element is slidably arranged in the locking device.

Due to the slidable design of the clamping element, there is no more need to perform a screwing motion on the clamping element by the hand of an operator. Therefore, unnecessary pressure on the uterus tissue which is caused by a twisting of the manipulator during the tightening of a screw-mechanism can be avoided.

Such a clamping element can thereby take any shape known to the man of the art. Examples for such clamping elements include sliding bolts, arranged transverse to the actuator, clamping wedges, or clamping pads which act on the actuator from one or more sides. The only condition for a use in an instrument according to the present invention being that the clamping element can be moved via the handle between a clamping and a non-clamping position by a sliding motion instead of a turning motion.

In an embodiment of the invention, the clamping element is realized as a bolt which is arranged transverse to the actuator.

The realization of the clamping element as a bolt is a mechanically particularly simple shape making production cheap. A bolt is nevertheless mechanically strong enough to ensure a secure clamping.

In a further embodiment of the above measure, the bolt comprises a bore through which the actuator extends.

Such a measure opens the possibility of using the inner surface of the bore as a large area clamping surface.

Further, this embodiment enables one to design the locking mechanism, in such a way that a lock can be achieved with a movement of the handle in two opposing directions, since the transverse bolt can be applied from two sides.

In a further embodiment of the invention, the clamping element is movable backwards and forwards between a first and a second position in a linear motion.

In an embodiment of the invention, the handle is realized as a pivoting lever.

The realization of the handle as a pivoting lever makes it possible to arrange it in such fashion that the grip of the medical instrument can be held with one hand, and the clamping element can be opened and closed with a finger of that hand.

This way, such a medical instrument can be operated in a most economic fashion with a single hand, whereby the positioning accuracy and the maintenance of the desired position of the medical instrument in a body of a patient is ascertained.

The locking device thereby especially comprises a coupling device which converts the pivoting motion of the pivoting lever into a linear motion of the clamping element.

The above measures are again characterized by a particular mechanical simplicity and a particular user friendliness. The coupling device can thereby take any shape known to the man of the art. It is, for example, possible to realize the coupling device in the shape of a combination of an internal and an external screw thread, in the shape of a combination of a screw thread and a rack, in the shape of a bolt within a groove, or in the shape of wedges sliding past each other.

This measure further has the advantage that it is possible to apply a relatively large amount of pressure to the actuator with a relatively small pivoting motion of the lever, ascertaining a safe locking of the actuator without transmitting excessive force onto the medical instrument which would be transmitted onto the tissue of a patient where it can lead to injury.

In a further embodiment of the above measure, the coupling device is formed by an internal screw thread and an external screw thread, whereby one of the screw threads is connected to the handle and the other screw thread is connected to the clamping element. Preferably, the internal and/or the external screw thread are realized as multiple threads.

In this embodiment of the invention, the lever is arranged on a pivoting axle. If the handle is pivoted around the pivoting axle, the internal screw thread is turned relatively to the external screw thread. If the clamping element is locked against rotation in the locking device, the external screw thread cannot follow this turning motion and is, therefore, moved within the locking device in a linear motion. This way, a positional change of the clamping element in relation to the actuator can be caused, and the actuator can, for example, be locked in the locking device.

The ergonomically favorable pivoting motion of the lever in the direction of the longitudinal axis is pleasant for a doctor and does not lead to a tilting or twisting.

This is elegantly transformed into a transverse motion of the transverse bolt in order to achieve a lock.

If the screw threads are realized as multiple threads, the step size by which the clamping element is moved for each pivoting motion can be adjusted individually. Only a much shortened screw movement is thereby necessary.

In a further embodiment of the invention, the grip is realized as a pistol grip.

The combination of the realization of the handle as a pivoting lever and the grip as a pistol grip, has been shown to be ergonomically particularly favorable. The grip can be held with one hand, while the pivoting lever is arranged in such a fashion that a finger of this hand can be used to actuate the pivoting lever. This way, the grip can be held securely, and yet the handle is easy to actuate.

In a further embodiment of the invention, the instrument is realized as a uterus manipulator.

The rodlike manipulator is used after insertion to move the uterus. This demands significant force. The moved uterus exerts strong restoring forces onto the tool. This necessitates a firm lock of the manipulator.

Due to the high restoring forces, the locking device should be as quick and easy to use as possible, so that an operator can concentrate fully on the positioning of the manipulator.

By using a locking device according to the invention, the locking device can be opened and closed with one hand in a simple way, whereby a secure locking of the instrument in the desired position remains assured. Thereby, the above problems can be solved.

It will be appreciated that the afore-mentioned measures and those still to be explained below can be applied not only in the specified combinations, but also in other combinations or in isolation, without departing from the scope of the present invention.

BRIEF DESCRIPTION OF THE DRAWINGS

The invention is described in greater detail and explained below on the basis of a chosen illustrative embodiments and in connection with the attached drawings, in which FIG. 5 shows the sectional view of FIG. 4 in closed position.

DETAILED DESCRIPTION OF A PREFERRED EMBODIMENT

In the following description, the expression "open position" means that the actuator is freely movable. The expression "closed position" means that the actuator is locked within the locking device.

Figure 1:
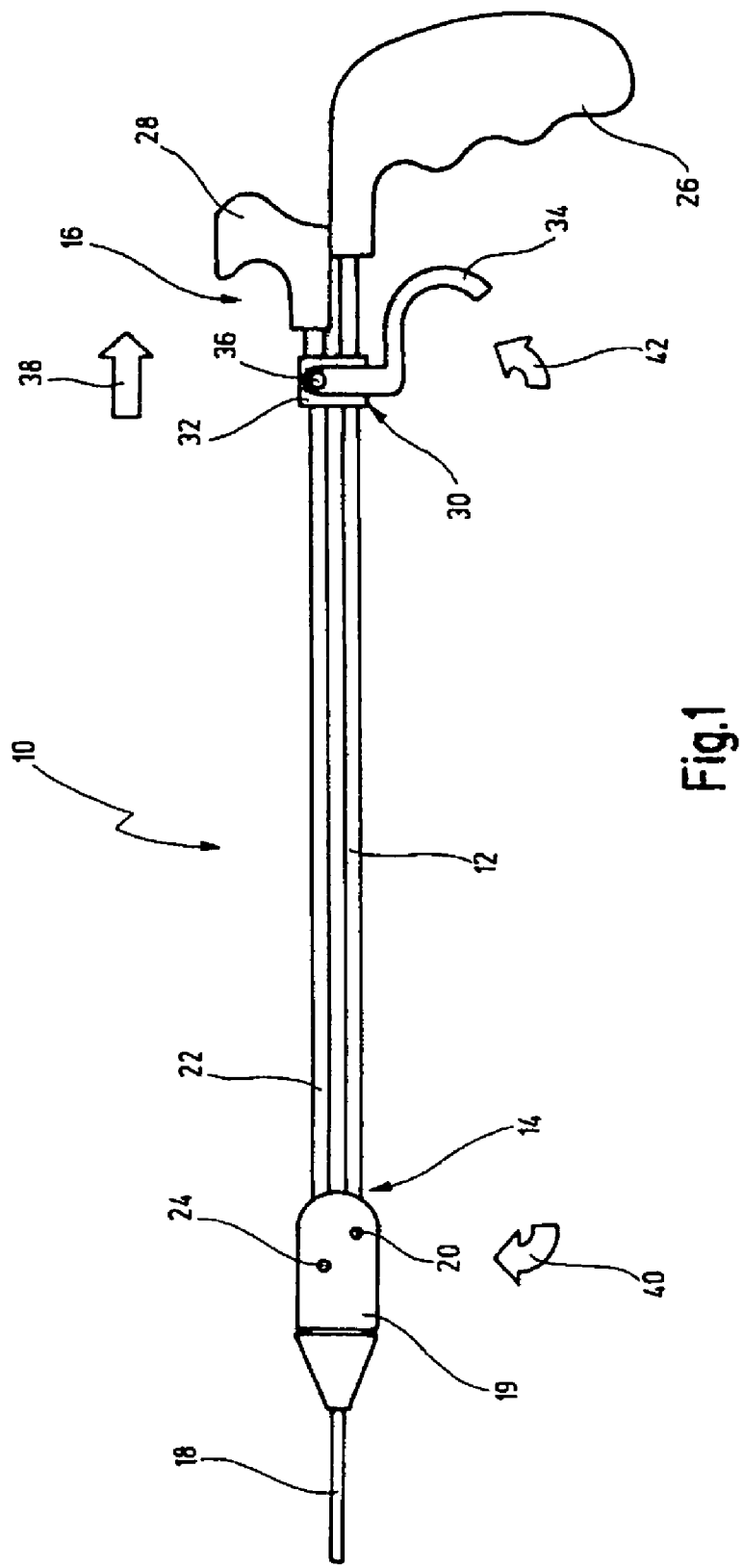
FIG. 1 shows a side view of a uterus manipulator.

In FIG. 1, a medical instrument in the shape of a uterus manipulator is designated in its entirety with the reference numeral 10.

The uterus manipulator 10 comprises a long shaft 12 with a distal end 14 and a proximal end 16. At the distal end there is arranged a tool 18 which, for example, serves during a laparoscopic examination to move the uterus of a female patient into a desired position.

The tool 18 is connected pivotably to the shaft 12 by a bolt 20 and can be deflected relative to the shaft 12 around bolt 20. (See transition from FIG. 1 to FIG. 2)

An actuator 22 extends parallel to shaft 12 and is connected on its proximal end to a tool holder 19 via a bolt 24. By means of the actuator 22, the tool 18 can be pivoted relative to the shaft 12.

At the distal end 14 of the shaft 12, a grip 26 is arranged which is realized here as a pistol grip. Above the grip 26, there is arranged a pull 28 which is connected to the actuator 22.

By means of the pull 28, the actuator 22 can be moved forwards and backwards parallel to shaft 12, thereby pivoting the tool 18 relative to shaft 12.

Figure 3:
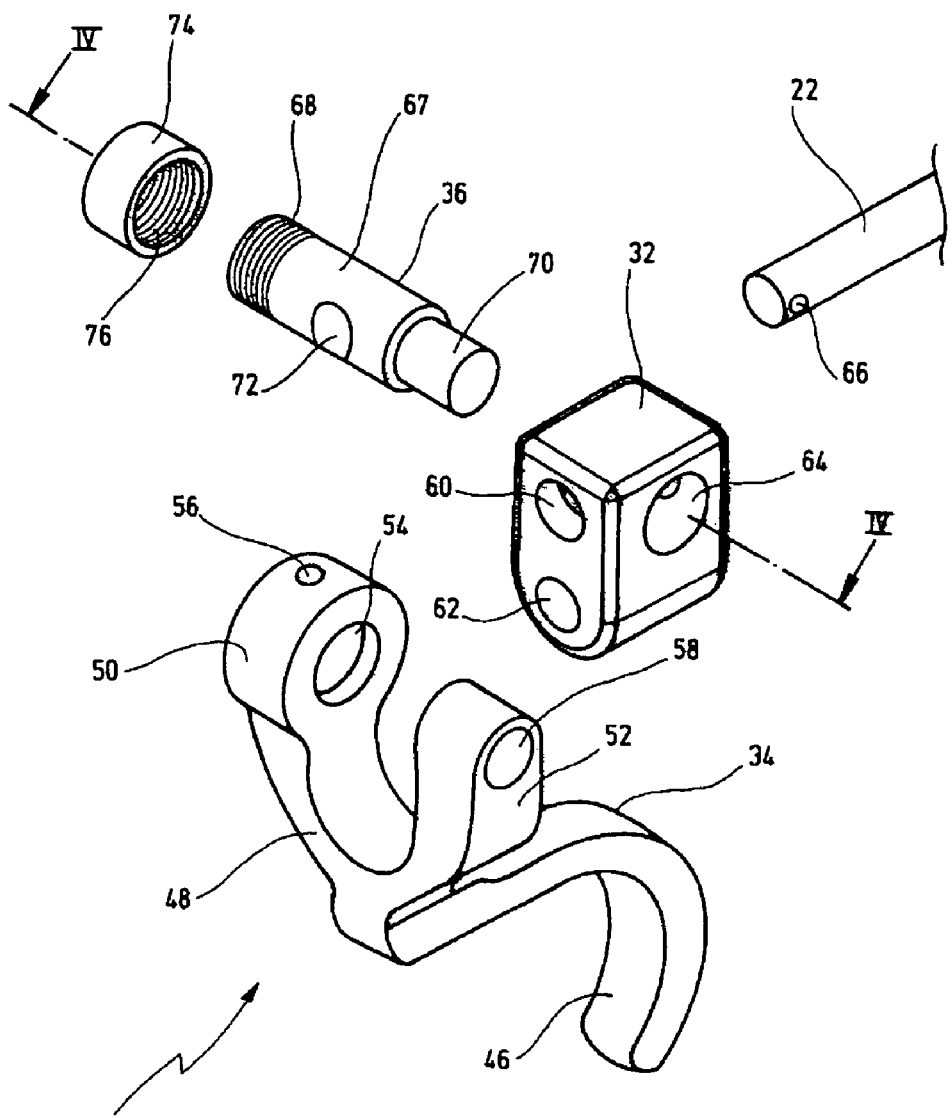
FIG. 3 shows an exploded view of the locking device of the uterus manipulator of FIG. 1.

The uterus manipulator 10 further comprises a locking device 30 (also see FIG. 3).

The locking device 30 comprises a body 32 through which the shaft 12 as well as the actuator 22 extend. The locking device 30 further comprises a handle 34 which is realized here as a pivoting lever. The handle 34 is shaped like a trigger, ergonomically matching the pistol grip 26.

The handle 34 is pivotable around bolt 36 relative to the body 32.

In use, the tool 18 of the uterus manipulator 10 is inserted into the uterus of a female patient and is pivoted relative to shaft 12 by pulling the pull 28 back in the direction indicated by arrow 38.

When the pull 28 is moved relative to the pistol grip 26 in the direction indicated by the arrow 38, the bolt 24 which connects the actuator 22 to the tool 18 moves relative to the bolt 20 which connects the tool 18 to the shaft 12. Since the bolt 20 is fixed, the linear motion of bolt 24 in relation to bolt 20 is converted to a pivoting motion of the tool 18 as indicated by arrow 40.

When the tool 18 has reached the desired position, the handle 34 can be pivoted relative to the body 32 of the locking device 30 in the direction indicated by arrow 42. This way, the actuator 22 is locked in its position relative to the shaft 12, and the tool 18 is held fast at a desired angle.

Figure 2:
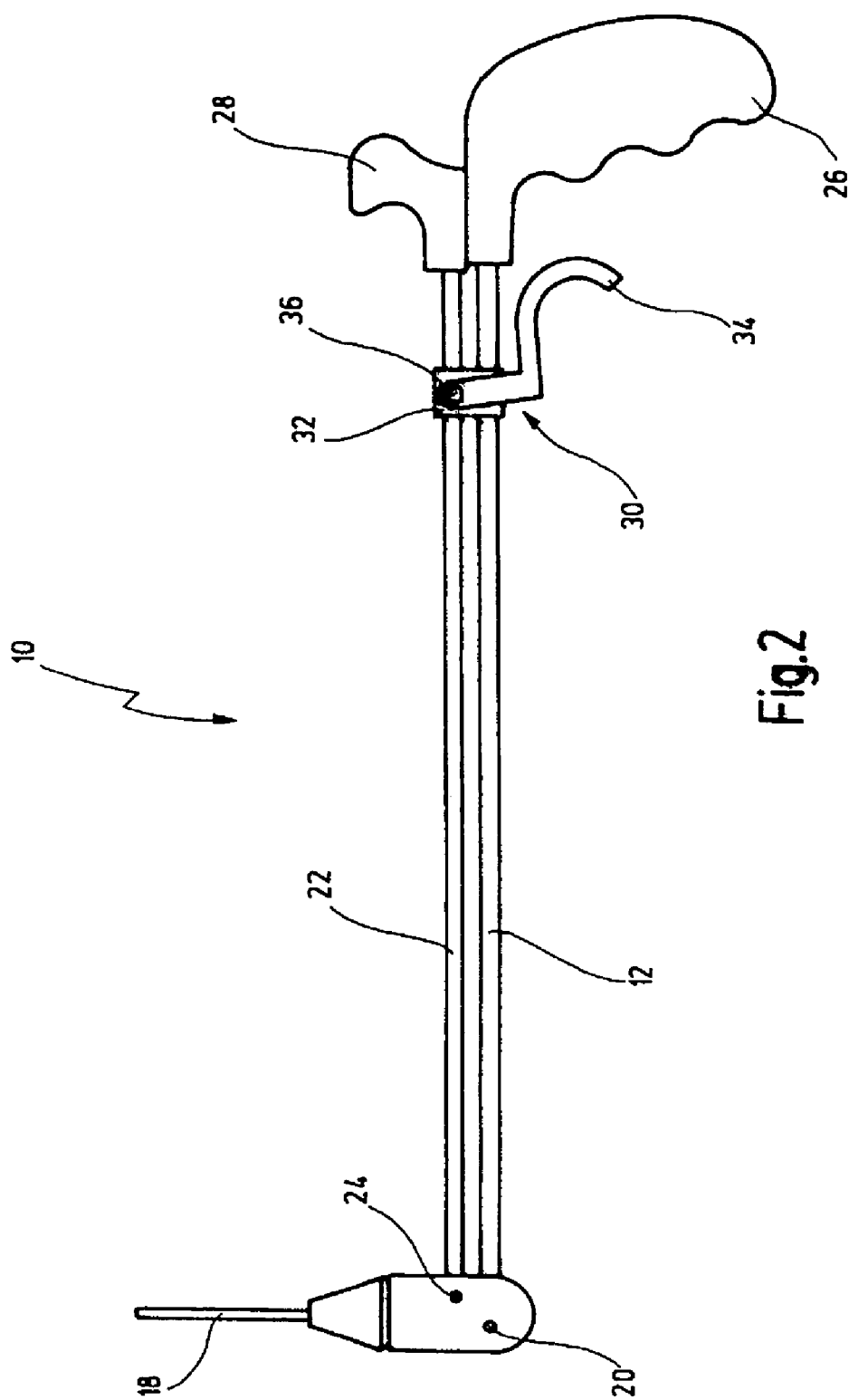
FIG. 2 shows the uterus manipulator of FIG. 1 with the tool in a deflected position.

In FIG. 2, the uterus manipulator 10 is shown in a second position after the movements indicated by the arrows of FIG. 1.

It is thereby visible that the tool 18 was pivoted by approximately 90° relative to shaft 12.

The handle 34 was pivoted around bolt 36 relative to the body 32 of the locking device 30. Thus, the locking device 30 is now in closed position, and the actuator 22 is locked relative to the shaft 12 in its present position.

FIG. 3 shows an exploded view of the locking device 30 of the uterus manipulator 10.

It becomes apparent here that the handle 34 comprises a curved section 46 and a forked section 48. The forked section 48 comprises a first prong 50 and a second prong 52.

The first prong 50 comprises a first bore 54 and a second bore 56, whereby the bore 56 extends approximately at right angles to bore 54.

The second prong 52 comprises a bore 58 which aligns with bore 54.

The body 32 of the locking device 30 is shaped in such a way that it can be inserted between the prongs 50 and 52 of the handle 34.

The body 32 comprises a bore 60 into which the actuator 22 whose distal section is not shown here can be inserted. A second bore 62 runs parallel to bore 60 through the body 32 and is designed to receive the shaft 12 of the uterus manipulator 10.

Furthermore, a bore 64 extends through the body 32 and runs transverse to the bore 60 and 62, respectively. The longitudinal axis of the bore 64 thereby intersects the longitudinal axis of the bore 60.

The distal end of the actuator 22 hereby further comprises a bore 66 which serves to connect the actuator 22 to the tool holder 19.

The transverse bolt 36 comprises a body 67 with a screw section 68 at one end and a section 70, having a smaller diameter than the body 67 of the bolt 36 at the other end. The bolt 36 further comprises a bore 72, whereby the longitudinal axis of the bore 72 runs approximately at right angles to the longitudinal axis 67 of the bolt 32.

The locking device 30 further comprises a nut 74 having an internal screw thread 76 on its inside. The internal screw thread 76 of the nut 74 and the screw section 68 of the bolt 36 are hereby realized as multiple threads. Therefore, only a small amount of force is needed to tighten it to the limit, and the pivoting angle is significantly reduced.

For assembly, the body 32 is inserted into the forked section 48 of the handle 34. Thereafter, the bolt 36 is threaded through the bore 54 of the first prong 50 of the forked section 48 and the bore 64 of the body 32, whereby the section 70 of the body 67 of the bolt 36 comes to rest in the bore 58 of the second prong 52 of the forked section 48.

The distal end of the actuator 22 is now threaded through the bore 60 of the body 32, and, therefore, through the bore 72 of the bolt 36. The nut 74 is screwed onto the screw section 68 of the bolt 36 coming to rest in the bore 54.

The nut 74 is connected tightly to the first prong 50 via a set screw which is screwed into the bore 56 of the first prong 50 of the forked section 48.

Figure 4:
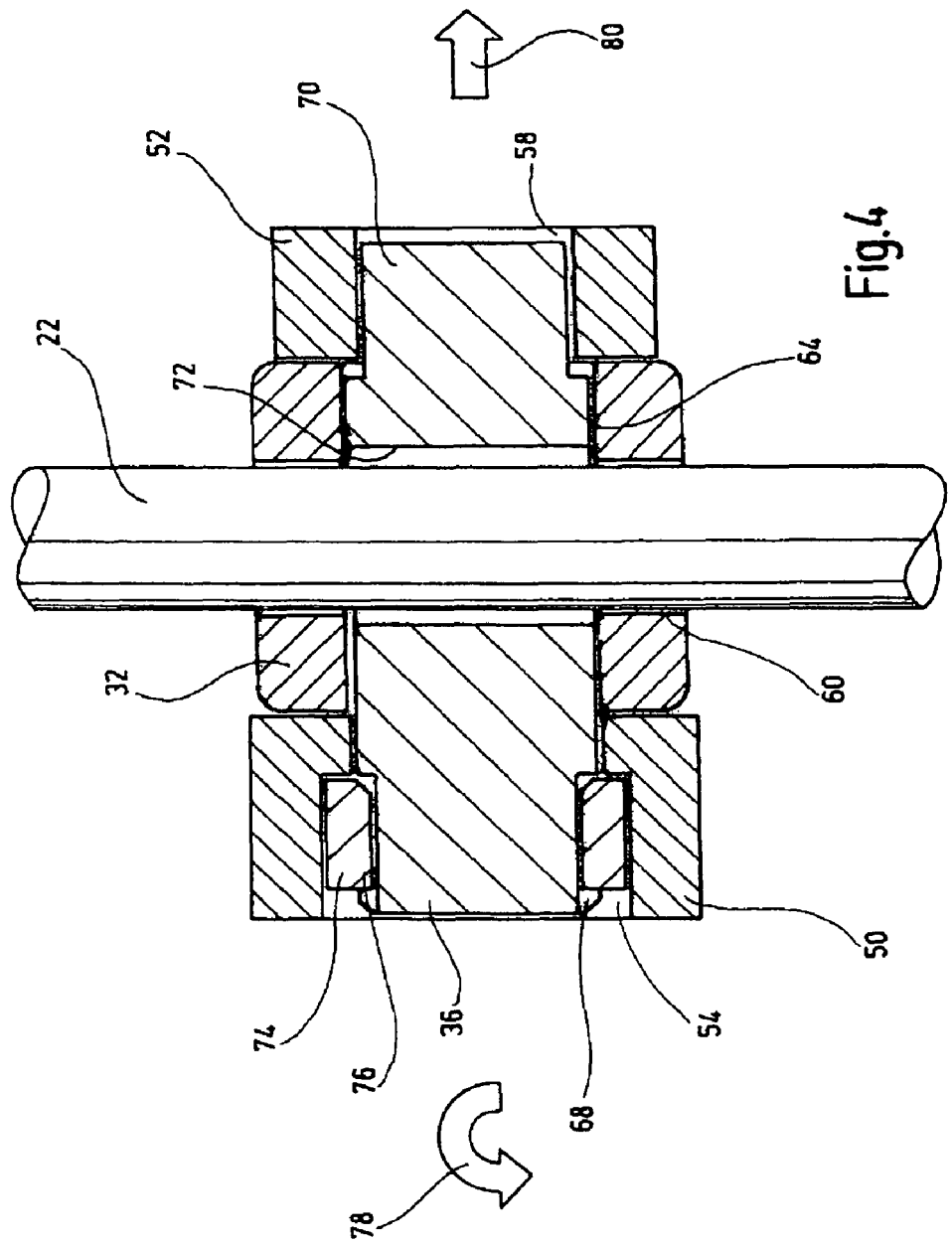
FIG. 4 shows a sectional view of the locking device of the uterus manipulator of FIG. 3 along the line IV-IV in open position.

FIG. 4 shows a sectional view of the assembled locking device 30 of FIG. 3 in open position.

This drawing shows that the bolt 36 extends through the bore 64 of the body 32. The screw section 68 of the bolt 36 thereby comes to rest in the bore 54 of the first prong 50 and is held therein by the nut 74. The section 70 of the body 67 of the bolt 36 comes to rest in the bore 58 of the second prong 52.

The bore 72 of the bolt 36 runs thereby approximately coaxial to the bore 60 of the body 32. The actuator 22 is arranged freely movable within the bore 60 of the body 32 and the bore 72 of the bolt 36, respectively.

When the handle 34 is now pivoted in the direction indicated by arrow 78, the first prong 50 of the forked section 48 and, therefore, the nut 74 is turned in the direction indicated by the arrow 78 around the longitudinal axis of the bolt 36. Due to the fact that the actuator 22 extends through the bore 72 of the bolt 36, the latter cannot follow this turning motion of the prong 50 and thereby the nut 74. The first prong 50 and, therefore, the nut 74 are then turned relatively to the bolt 36. Due to the engagement of the internal screw thread 76 of the nut 74 with the screw section 68 of the bolt 36, the latter is moved in the direction indicated by arrow 80.

The internal screw thread 76 of the nut 74 and the screw section 68 of the bolt 36 are thereby self-locking. This means, the bolt 36 will remain in the closed position after the actuation of handle 34. To return the bolt 36 to the open position, the handle 34 must be moved in the opposite direction.

FIG. 5 shows the sectional view of FIG. 4 in closed position.

It can thereby be seen that the bolt 36 was moved relative to body 32. One side of the bore 72 of the bolt 36 now pushes against the actuator 22. The actuator 22 is thus pushed against the bore 60 of the body 32 on the side which is opposite the contact surface between the bore 72 and the actuator 22. This way, the actuator 22 is securely locked within the bore 60 of the body 32 and can no longer move in the directions indicated by double-headed arrow 82.

What is claimed is:

1. A medical instrument comprising:
a shaft having a distal end and a proximal end,
a tool at said distal end of said shaft,
a grip at said proximal end of said shaft,
an actuator with which said tool is movable, and
a locking device comprising a pivoting lever and a clamping element, said clamping element being movable by said pivoting lever between a first and a second position, whereby in said first position of said clamping element said actuator is freely movable, and in said second position of said clamping element said actuator is locked in said locking device,
said clamping element being slidably arranged in said locking device.

2. The instrument of claim 1, wherein said clamping element is realized as a bolt which is arranged transverse to said actuator.

3. The instrument of claim 2, wherein said bolt comprises a bore through which said actuator extends.

4. The instrument of claim 1, wherein said clamping element is movable backwards and forwards between said first and said second position by a linear motion.

5. The instrument of claim 1, wherein said locking device comprises a coupling device with which a pivoting motion of said pivoting lever is converted into a linear motion.

6. The instrument of claim 5, wherein said coupling device is formed by an internal screw thread and an external screw thread, whereby one of said screw threads is connected to said pivoting lever, and the other of said screw threads is connected to said clamping element.

7. The instrument of claim 6, wherein said internal screw thread and/or said external screw thread are realized as multiple threads.

8. The instrument of claim 1, wherein said grip is realized as a pistol grip.

9. The instrument of claim 1, wherein said pivoting lever is arranged in the vicinity of said grip such that it can be actuated by a finger of a hand holding said grip.

10. The instrument according to claim 1, wherein said instrument is realized as a uterus manipulator.

* * * * *